US011059779B2

(12) United States Patent
Gerritsen et al.

(10) Patent No.: US 11,059,779 B2
(45) Date of Patent: Jul. 13, 2021

(54) STORAGE STABLE AQUEOUS ORGANIC PEROXIDE EMULSIONS

(71) Applicant: NOURYON CHEMICALS INTERNATIONAL B.V., Arnhem (NL)

(72) Inventors: René Gerritsen, Loosdrecht (NL); Richard Hermannes Johannes Hekkert, Deventer (NL); Ester Elisabeth Antonia Keijzer, Deventer (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/083,904

(22) PCT Filed: Mar. 14, 2017

(86) PCT No.: PCT/EP2017/055932
§ 371 (c)(1),
(2) Date: Sep. 11, 2018

(87) PCT Pub. No.: WO2017/157904
PCT Pub. Date: Sep. 21, 2017

(65) Prior Publication Data
US 2019/0071397 A1    Mar. 7, 2019

(30) Foreign Application Priority Data
Mar. 18, 2016 (EP) .................................... 16161148

(51) Int. Cl.
*C07C 407/00* (2006.01)
*C08F 2/22* (2006.01)
*C08F 2/40* (2006.01)
*C08F 4/34* (2006.01)
*C08F 14/06* (2006.01)
*C07C 409/36* (2006.01)
*C07C 409/38* (2006.01)

(52) U.S. Cl.
CPC ............ *C07C 407/006* (2013.01); *C08F 2/22* (2013.01); *C08F 2/40* (2013.01); *C08F 4/34* (2013.01); *C08F 14/06* (2013.01); *C07C 409/36* (2013.01); *C07C 409/38* (2013.01)

(58) Field of Classification Search
CPC .................... C08F 2/40; C08F 4/34
See application file for complete search history.

(56) References Cited

U.S. PATENT DOCUMENTS

| 6,350,835 B1 | 2/2002 | O et al. |
| 7,214,329 B2 | 5/2007 | O |
| 7,973,194 B1 | 7/2011 | Kinkade et al. |
| 2004/0132938 A1* | 7/2004 | O ........................ C07C 407/006 526/230 |
| 2011/0318292 A1* | 12/2011 | Phelan .................... C07C 69/28 424/70.1 |
| 2015/0322182 A1 | 11/2015 | Spies et al. |

FOREIGN PATENT DOCUMENTS

| CA | 2376742 A1 | 12/2000 |
| CN | 1498207 A | 5/2004 |
| CN | 101774919 A | 7/2010 |
| EP | 1144461 B1 | 3/2004 |
| EP | 2 810 982 A1 | 12/2014 |
| JP | S62-86005 A | 4/1987 |
| JP | H11171914 A | 6/1999 |
| JP | 2001510859 A | 8/2001 |
| JP | 2003503526 A | 1/2003 |
| JP | 2013522293 A | 6/2013 |
| RU | 2232776 C2 | 7/2004 |
| RU | 2285011 C2 | 10/2006 |
| WO | 9905101 A1 | 2/1999 |
| WO | 9931194 A1 | 6/1999 |
| WO | 02/076936 A1 | 10/2002 |
| WO | 2014195056 A1 | 12/2014 |

OTHER PUBLICATIONS

European Search Report issued in the counterpart European Application No. 16161148.8 dated Aug. 26, 2016.
Notification of Transmittal of the International Search Report and the Written Opinion of the International Searching Authority, or the Declaration from the International Bureau of WIPO for International Application No. PCT/EP2017/055932 dated May 23, 2017.
SIPO, Chinese Search Report issued in Chinese Application No. 201780016503X, dated Sep. 30, 2019.
RUPTO, Russian Search Report issued in Russian Application No. 2018135745, dated Apr. 1, 2020.

* cited by examiner

*Primary Examiner* — Peter F Godenschwager
(74) *Attorney, Agent, or Firm* — Lorenz & Kopf, LLP

(57) ABSTRACT

Aqueous emulsion comprising: —25-70 wt % organic peroxide, based on the weight of the emulsion, —a cyclohexane dicarboxylate ester, and —water. This emulsion is storage stable and can be used for the production of polymers, in particular PVC, that come into contact with food products.

20 Claims, No Drawings

STORAGE STABLE AQUEOUS ORGANIC PEROXIDE EMULSIONS

This application is a national stage filing under 35 U.S.C. § 371 of PCT/EP2017/055932, filed Mar. 14, 2017, which claims priority to European Patent Application No. 16161148.8, filed Mar. 18, 2016, the contents of which are each incorporated herein by reference in their entireties.

The present invention relates to an aqueous organic peroxide emulsion and its use in the polymerization of vinyl chloride.

As is well known, organic peroxides are thermally labile compounds. Because the decomposition of these peroxides is exothermic, it is hazardous when the heat of decomposition cannot be dissipated, e.g., by heat loss to the surrounding area. When heat accumulates, the decomposition reaction may run out of control. To avoid such undesired situation, the peroxide typically is formulated with one or more phlegmatising agents. One example of a phlegmatizing agent is water.

Aqueous organic peroxide emulsions are generally considered safe products because the peroxide is dispersed—forming small droplets—in the water phase, which water phase is well-suited for the removal of the heat of decomposition by, for instance, convection and/or evaporation.

However, many aqueous organic peroxide emulsions are not sufficiently stable upon storage. Most aqueous organic peroxide emulsions used commercially are stored at low temperatures, typically −25° C. to 0° C. Although emulsion formulations are well optimised with respect to viscosity and droplet size, droplet growth remains a problem, resulting in a short emulsion shelf life time. The growth of droplets may (eventually) result in layer separation of the emulsion, causing a formulation which was thought to be safe to become unsafe. Moreover, in a number of applications, for instance in the manufacture of PVC, the number of fish eyes increases with emulsion age.

JP-A-62086005 relates to an aqueous organic peroxide emulsion comprising a partially saponified polyvinyl acetate with a saponification degree of 5 to 70 mole % as an emulsification stabiliser. By using the partially saponified polyvinyl acetate, layer separation of the emulsion—which is the worst form of emulsion instability—could be prevented. It is described that the stability of the emulsion could be improved further by adding a hydrocarbon-based solvent such as n-hexane, toluene, xylene or IP (iso-paraffin) solvent, a plasticiser such as DBP (dibutyl phthalate), DOP (dioctyl phthalate), and DOA (dioctyl adipate), or a chlorine-based solvent such as methylene chloride, carbon tetrachloride, and tetrachloroethylene. Examples are given using DOP and carbon tetrachloride. A relatively large amount of DOP and carbon tetrachloride (i.e. 10 wt %) appears to have been used in order to obtain the improved emulsion stability.

As discussed in WO 2002/076936, aqueous organic peroxide emulsions comprising the above plasticizers still suffer from instability, i.e. droplet growth upon storage. The use of a plasticizer with an Ap/Po ratio higher than 8, however, resulted in a higher stability. The Ap/Po ratio refers to the ratio of the number of carbon atoms present in the plasticiser molecule (excluding aromatic carbon atoms and the carbon atoms of the ester groups) to the number of ester groups in the molecule. Preferred plasticizers are phthalates and adipates; more in particular diisononyl phthalate, diisodecyl phthalate, diisoundecyl phthalate, diisododecyl phthalate, and diisodecyl adipate.

Today's legislation does no longer allow the above adipates and phthlates to be present in polymers that come into contact with food products. Hence, there is need for stable organic peroxide emulsions that can be used for the production of polymers, in particular PVC, that come into contact with food products.

It has now been found that this object can be achieved by using a cyclohexane dicarboxylate ester as droplet growth inhibitor.

The present invention therefore relates to an aqueous emulsion comprising:
25-70 wt % organic peroxide, based on the weight of the emulsion,
a cyclohexane dicarboxylate ester, and
water.

Cyclohexane dicarboxylate esters are food contact approved and are already known as plasticizer in PVC. That they are also suitable as droplet growth inhibitor in peroxide emulsions is, however, surprising.

Examples of suitable cyclohexane dicarboxylate esters are:
di-alkyl-cyclohexane-1,2-dicarboxylates, such as di-n-octyl cyclohexane-1,2-dicarboxylate, diisooctyl cyclohexane-1,2-dicarboxylate, di-2-ethylhexyl cyclohexane-1,2-dicarboxylate, di-n-nonyl cyclohexane-1,2-dicarboxylate, diisononyl cyclohexane-1,2-dicarboxylate, di-n-decyl cyclohexane-1,2-dicarboxylate, diisodecyl cyclohexane-1,2-dicarboxylate, di-n-undecyl cyclohexane-1,2-dicarboxylate, diisododecyl cyclohexane-1,2-dicarboxylate, di-n-octadecyl cyclohexane-1,2-dicarboxylate, diisooctadecyl cyclohexane-1,2-dicarboxylate, di-n-eicosyl cyclohexane-1,2-dicarboxylate, monocyclohexyl cyclohexane-1,2-dicarboxylate, dicyclohexyl cyclohexane-1,2-dicarboxylate di-n-hexyl cyclohexane-1,2-dicarboxylate, diisohexyl cyclohexane-1,2-dicarboxylate, di-n-heptyl cyclohexane-1,2-dicarboxylate, diisoheptyl cyclohexane-1,2-dicarboxylate, di-2-propylheptyl cyclohexane-1,2-dicarboxylate, diisoundecyl cyclohexane-1,2-dicarboxylate, di-n-dodecyl cyclohexane-1,2-dicarboxylate, di-n-tridecyl cyclohexane-1,2-dicarboxylate, diisotridecyl cyclohexane-1,2-dicarboxylate, di-n-pentyl cyclohexane-1,2-dicarboxylate, and diisopentyl cyclohexane-1,2-dicarboxylate,
di-alkyl-cyclohexane-1,4-dicarboxylates, such as di-n-octyl cyclohexane-1,4-dicarboxylate, diisooctyl cyclohexane-1,4-dicarboxylate, mono-2-ethylhexyl cyclohexane-1,4-dicarboxylate, di-2-ethylhexyl cyclohexane-1,4-dicarboxylate, di-n-nonyl cyclohexane-1,4-dicarboxylate, diisononyl cyclohexane-1,4-dicarboxylate, di-n-decyl cyclohexane-1,4-dicarboxylate, di-n-undecyl cyclohexane-1,4-dicarboxylate, diisodecyl cyclohexane-1,4-dicarboxylate, diisododecyl cyclohexane-1,4-dicarboxylate, di-n-octadecyl cyclohexane-1,4-dicarboxylate, diisooctadecyl cyclohexane-1,4-dicarboxylate, di-n-eicosyl cyclohexane-1,4-dicarboxylate, monocyclohexyl cyclohexane-1,4-dicarboxylate, dicyclohexyl cyclohexane-1,4-dicarboxylate, di-n-hexyl cyclohexane-1,4-dicarboxylate, diisohexyl cyclohexane-1,4-dicarboxylate, di-n-heptyl cyclohexane-1,4-dicarboxylate, diisoheptyl cyclohexane-1,4-dicarboxylate, di-2-propylheptyl cyclohexane-1,4-dicarboxylate, diisoundecyl cyclohexane-1,4-dicarboxylate, di-n-dodecyl cyclohexane-1,4-dicarboxylate, di-n-tridecyl cyclohexane-1,4- dicarboxylate, diisotridecyl cyclohexane-1,4-dicarboxylate, di-n-pentyl cyclohexane-1,4-dicarboxylate, diisopentyl cyclohexane-1,4-dicarboxylate; and di-alkyl cyclohexane-1,3-dicarboxylates, such as di-n-octyl cyclohexane-1,3-dicarboxylate, diisooctyl cyclohexane-1,3-dicarboxylate, di-2-ethylhexyl cyclohexane-1,3-dicarboxylate, di-n-nonyl cyclohexane-1,3-dicarboxylate, diisononyl cyclohexane-1,3-dicarboxylate, di-n-decyl cyclohexane-1,3-dicarboxylate, diisodecyl cyclohexane-1,3-dicarboxylate, di-n-undecyl cyclohexane-1,3-dicarboxylate, diisododecyl cyclohexane-1,3-dicarboxylate, di-n-octadecyl cyclohexane-1,3-dicarboxylate, diisooctadecyl cyclohexane-1,3-dicarboxylate, di-n-eicosyl cyclohexane-1,3-dicarboxylate, monocyclohexyl cyclohexane-1,3-dicarboxylate, dicyclohexyl cyclohexane-1,3-dicarboxylate, di-n-hexyl cyclohexane-1,3-dicarboxylate, diisohexyl cyclohexane-1,3-dicarboxylate, di-n-heptyl cyclohexane-1,3-dicarboxylate, diisoheptyl cyclohexane-1,3-dicarboxylate, di-2-propylheptyl cyclohexane-1,3-dicarboxylate, diisoundecyl cyclohexane-1,3-dicarboxylate, di-n-dodecyl cyclohexane-1,3-dicarboxylate, di-n-tridecyl cyclohexane-1,2-dicarboxylate, diisotridecyl cyclohexane-1,3-dicarboxylate, di-n-pentyl cyclohexane-1,3-dicarboxylate, and diisopentyl cyclohexane-1,3-dicarboxylate.

Preferably, the cyclohexane dicarboxylate esters is a di-alkyl cyclohexane-1,2-dicarboxylate. Most preferably, it is di-isononyl-1,2-cyclohexane dicarboxylate.

Emulsions are mixtures of two or more immiscible liquids, one being present in the other in the form of droplets. The present invention therefore relates to aqueous organic peroxide emulsions comprising an organic peroxide which is a liquid at storage and handling temperatures.

In the emulsion according to the present invention, the 99 percentile of the droplet volume distribution (d99) of the organic peroxide preferably does not exceed 15, more preferably 10, even more preferably 8, and most preferably 6 μm during 12 weeks of storage at −20° C. Changes in droplet volume distribution influence the viscosity and storage stability of the emulsion. Also the polymerisation process can be adversely affected when an emulsion with larger organic peroxide droplets is used, e.g., by having an increased number of fish eyes in the case of the production of PVC. The droplet volume distribution is determined in a conventional way by means of a light scattering technique, measured, for example, by using a Malvern type 3000 apparatus.

The amount of cyclohexane dicarboxylate ester required to optimise the storage stability of the aqueous organic peroxide emulsion according to this invention will depend on the type and amount of organic peroxide and the type of cyclohexane dicarboxylate ester. Typically, an amount of 0.1 to 10, preferably 0.5 to 5, more preferably, 0.5 to 3, most preferably 0.5 to 2 wt %, based on the total weight of the emulsion, is used.

The organic peroxides that can be formulated in accordance with the present invention are liquid organic peroxides, more preferably polar liquid organic peroxides. The group of liquid organic peroxides includes hydroperoxides, peroxyesters, peroxycarbonates, peroxydicarbonates, diacyl peroxides, dialkyl peroxides, and bis(acylperoxy)alkanes. Preferred are peroxyesters and diacyl peroxides.

Examples of preferred organic peroxides for use in accordance with the present invention are diisobutyryl peroxide, cumyl peroxyneodecanoate, 1,1,3,3-tetramethylbutyl peroxyneodecanoate, tert-amyl peroxyneodecanoate, tert-butyl peroxyneodecanoate, dibutyl peroxydicarbonate, 1,1,3,3-tetramethylbutyl peroxy-2-ethylhexanoate, 1,1,3,3-tetramethylbutyl peroxypivalate, tert-butyl peroxyneoheptanoate, tert-amyl peroxy-2-ethyl hexanoate, tert-amyl peroxypivalate, tert-butyl peroxy-2-ethyl hexanoate, tert-butyl peroxypivalate, tert-butyl peroxydiethylacetate, tert-butyl peroxyisobutyrate, di(2-ethylhexyl) peroxydicarbonate, di(3,5,5-trimethylhexanoyl) peroxide, 2,5-dimethyl-2,5-di(2-ethylhexanoylperoxy)hexane, 1-hydroperoxy-1,3-dimethylbutyl peroxypivalate, 1-(2-ethyl hexyl peroxy)-1,3-dimethylbutyl peroxypivalate, 2-(2-ethylhexanoylperoxy)-2-(pivaloylperoxy)-4-methyl-pentane, and 2-(2-ethylhexyloxycarbonylperoxy)-2-(isobutanoylperoxy)-5-methyl-hexane.

More preferably, the organic peroxide to be used in accordance with the present invention is selected from the group consisting of cumyl peroxyneodecanoate, tert-butyl peroxyneodecanoate, diisobutyryl peroxide, 1,1,3,3-tetramethylbutyl peroxyneodecanoate, tert-amyl peroxyneodecanoate, di(2-ethylhexyl) peroxydicarbonate, di-sec-butyl peroxydicarbonate, tert-butyl peroxyneoheptanoate, tert-amyl peroxypivalate, tert-butyl peroxypivalate, di(3,5,5-trimethylhexanoyl) peroxide, 1-(2-ethylhexylperoxy)-1,3-dimethylbutyl peroxypivalate, and (2-(2-ethylhexanoylperoxy)-2-(pivaloylperoxy)-4-methylpentane. Most preferably, the organic peroxide to be used in accordance with the present invention is selected from the group consisting of cumyl peroxyneodecanoate, tert-butyl peroxyneodecanoate, tert-butyl peroxyneoheptanoate, and 1-(2-ethylhexylperoxy)-1,3-dimethylbutyl peroxypivalate, and di(3,5,5-trimethylhexanoyl) peroxide.

The aqueous organic peroxide emulsion of the present invention contains 25-70 wt % of organic peroxide, based on the total weight of the emulsion. Preferably, the amount of organic peroxide in the emulsion is 30-65 wt %, more preferably 35-60 wt %, most preferably 40-60 wt %.

The amount of water in the emulsion preferably ranges from 20-70 wt %, more preferably 25-50 wt %, and most preferably 25-40 wt %.

The emulsion preferably also contains an anti-freeze agent.

Any conventional anti-freeze agent can be used. Preferably, use is made of methanol, ethanol, isopropanol, (ethylene) glycol, propanediol, glycerol, and mixtures thereof, more preferably, methanol, ethanol, propanediol and mixtures thereof. These agents are known to have hardly any effect on polymerisation processes. A skilled person will have no difficulties in balancing the ratio of water to anti-freeze agent(s). Typically, the amount of anti-freeze agent used in the emulsion according to the present invention will be lower than the amount of water. Preferred water/anti-freeze weight ratios range between 3/1 and 2/1.

The emulsion preferably also contains a protective colloid.

Any conventional protective colloid can be used. Suitable protective colloids include partially hydrolysed (or saponified) polyvinyl acetates, polyvinyl pyrrolidones, polyacrylates, cellulose, cellulose derivatives, starch, and starch derivatives. Particularly useful are partially hydrolysed/saponified polyvinyl acetates, cellulose, cellulose derivatives, starch, and starch derivatives. Typically, a polyvinyl acetate (PVA), preferably having a degree of hydrolysis of 50-75 mole %, is used.

The amount of protective colloid used in the emulsions according to the present invention will depend on the type and amount of organic peroxide and the desired viscosity of the final emulsion. Typically, the amount of protective colloid in the final emulsion will be between 0.5 and 10 wt %, preferably between 0.5 and 5 wt %, more preferably between 0.5 and 3 wt %, most preferably between 0.5 and 2 wt %, based on the total weight of the emulsion.

Preferably, the emulsion in accordance with the present invention further contains a conventional emulsifier. Suitable emulsifiers are known to the person skilled in this art and they include non-ionic, anionic, cationic, and amphoteric surfactants, and mixtures thereof. They may be incorporated in their usual amounts. Preferably, a non-ionic surfactant, more preferably having an HLB (hydrophile-lipophile balance) value of 7 or higher, even more preferably 16 or higher, is used.

The aqueous organic peroxide emulsions of the present invention optionally may also contain other additives including pH-adjusting agents such as phosphate and citrate buffers, sequestering agents, biocides, e.g. fungicides, antiozonants, antioxidants, antidegradants, U.V. stabilisers, coagents, comonomers, antistatic agents, blowing agents, mould release agents, and process oils. These additives may be added in their usual amounts.

The emulsions of the present invention can be produced in a conventional manner. Typically, the ingredients of the emulsion are mixed and/or homogenised using well-known equipment, such as high-speed mixers, colloid mills, pearl mills, ball mills, pressure homogenisers, fluidisers, and ultrasonic homogenisers. Because many of the organic peroxides which are used in accordance with the present invention are not stable at higher temperatures, the mixing and/or homogenising typically is carried out below a temperature of 15° C., preferably, well below the self-accelerating decomposition temperature (SADT) of the organic peroxide.

The present invention also relates to the use of the above-described aqueous organic peroxide emulsions in polymerisation processes, cross-linking reactions, the curing of unsaturated polyester resins, polymer modification processes, and other reactions involving free radicals, like the synthesis of certain chemicals.

The emulsions of the present invention preferably are used in polymerisation processes, more preferably, the polymerisation of vinyl chloride monomer (VCM) and copolymerisation of VCM with styrene or (meth)acrylate. Most preferred is the use of the emulsion in accordance with the present invention in a suspension polymerisation process for preparing PVC.

The present invention is further illustrated by the following Examples.

EXAMPLES

General Procedure

In the following Examples, the aqueous organic peroxide emulsions were made by the following general procedure: to a cooled vessel at −10° C. were added organic peroxide (final content is 50 wt %, based on the total weight of the emulsion), PVA (polyvinyl acetate, degree of hydrolysis 62.5-67.5%, ex Unitika), droplet growth inhibitor, plasticiser ester (see Tables), and non-ionic surfactant (C16/C18 ethoxylated alcohol), water, and methanol indicated in the Examples below. The organic peroxide was dispersed using an UltraTurrax type S25N-25GM (4 minutes/kg of emulsion) at full power, during which the temperature of the emulsion was kept below 15° C.

The droplet volume distribution was determined by means of a light scattering technique, using a Malvern type 3000 apparatus. In the Tables, d99 (expressed in μm) is 99 percentile of the droplet volume distribution of the organic peroxide in the emulsion; d50 (expressed in μm) is 50 percentile of the droplet volume distribution of the organic peroxide in the emulsion. The emulsion samples were stored at −20° C. and the data were collected at room temperature.

The viscosity was measured at −10° C. with a Brookfield LVT (spindle 3; at 12 and 30 RPM).

Example 1 and Comparative Examples A and B

Three emulsions were made according to the above procedure, using tert-butyl peroxyheptanoate as the peroxide and diisodecyl adipate (DIDA), dioctyl adipate (DOA), and di-isononyl cyclohexane dicarboxylate (DINCH) as the droplet growth inhibitor.

TABLE 1

| Example | A | B | 1 |
|---|---|---|---|
| Peroxide (wt %) | 50 | 50 | 50 |
| PVA (wt %) | 3.0 | 3.0 | 3.0 |
| Surfactant (wt %) | 0.5 | 0.5 | 0.5 |
| DIDA (wt %) | 0.9 | | |
| DOA (wt %) | | 0.9 | |
| DINCH (wt %) | | | 0.9 |
| MeOH (wt %) | 12.8 | 12.8 | 12.8 |
| Water (wt %) | 32.8 | 32.8 | 32.8 |
| Droplet size: | | | |
| 1 day - d50/d99 | 0.5/1.1 | 1.4/3.3 | 0.5/1.3 |
| 2 weeks - d50/d99 | 1.5/4.0 | 3.7/9.5 | 1.9/4.1 |
| 4 weeks - d50/d99 | | 5.8/15.0 | 2.2/5.9 |
| 8 weeks - d50/d99 | 2.4/5.4 | | 3.4/8.3 |
| 12 weeks - d50/d99 | 2.9/6.8 | | 3.9/9.6 |
| Viscosity (mPa · s): | | | |
| 1 day - 12/30 RPM | 720/616 | 410/400 | 720/616 |
| 2 weeks - 12/30 RPM | 360/332 | 290/280 | 310/292 |
| 4 weeks - 12/30 RPM | | 280/264 | |
| 8 weeks - 12/30 RPM | 350/340 | | 290/280 |
| 12 weeks - 12/30 RPM | 270/260 | | 220/200 |

This Table shows that DINCH is a very good droplet growth inhibitor. Its performance is comparable to that of DIDA and much better than that of DOA. The latter resulted in a d99>15 μm after 4 weeks.

In contrast to DIDA and DOA, DINCH is food contact approved.

Example 2 and Comparative Examples C and D

Example 1 and Comparative Examples A and B were repeated, except that tert-butyl peroxyneodecanoate was used as the peroxide.

TABLE 2

| Example | C | D | 2 |
|---|---|---|---|
| Peroxide (wt %) | 50 | 50 | 50 |
| PVA (wt %) | 2.8 | 2.8 | 2.8 |
| Surfactant (wt %) | 0.5 | 0.5 | 0.5 |
| DIDA (wt %) | 0.9 | | |
| DOA (wt %) | | 0.9 | |
| DINCH (wt %) | | | 0.9 |
| MeOH (wt %) | 12.7 | 12.7 | 12.7 |
| Water (wt %) | 33.1 | 33.1 | 33.1 |

TABLE 2-continued

| Example | C | D | 2 |
|---|---|---|---|
| Droplet size: | | | |
| 1 day - d50/d99 | 1.0/2.0 | 1.7/2.9 | 0.9/1.9 |
| 2 weeks - d50/d99 | 1.7/3.6 | 3.7/8.4 | 2.5/5.1 |
| 4 weeks - d50/d99 | | 4.9/12.0 | 3.2/6.5 |
| 8 weeks - d50/d99 | 3.2/7.1 | | 3.8/9.7 |
| 12 weeks - d50/d99 | 3.8/8.7 | | 4.0/9.9 |
| Viscosity (mPa · s): | | | |
| 1 day - 12/30 RPM | 560/516 | 460/440 | 550/496 |
| 2 weeks - 12/30 RPM | 350/348 | 310/292 | 280/260 |
| 4 weeks - 12/30 RPM | | 290/284 | |
| 8 weeks -12/30 RPM | 390/356 | | 240/323 |
| 12 weeks - 12/30 RPM | 290/280 | | 260/268 |

Example 3 and Comparative Examples E and F

Example 1 and Comparative Examples A and B were repeated, except that tert-amyl peroxyneodecanoate was used as the peroxide.

TABLE 3

| Example | E | F | 3 |
|---|---|---|---|
| Peroxide (wt %) | 50 | 50 | 50 |
| PVA (wt %) | 2.8 | 2.8 | 2.8 |
| Surfactant (wt %) | 0.5 | 0.5 | 0.5 |
| DIDA (wt %) | 0.9 | | |
| DOA (wt %) | | 0.9 | |
| DINCH (wt %) | | | 0.9 |
| MeOH (wt %) | 12.5 | 12.5 | 12.5 |
| Water (wt %) | 33.3 | 33.3 | 33.3 |
| Droplet size: | | | |
| 1 day - d50/d99 | 1.3/2.5 | 1.8/3.4 | 1.0/1.8 |
| 2 weeks - d50/d99 | 2.4/4.5 | 4.2/9.7 | 2.6/5.2 |
| 4 weeks - d50/d99 | | 6.1/12.4 | 3.5/7.3 |
| 8 weeks - d50/d99 | 3.5/7.8 | | 4.0/10.3 |
| 12 weeks - d50/d99 | 3.9/10.0 | | 4.9/12.0 |
| Viscosity (mPa · s): | | | |
| 1 day - 12/30 RPM | 780/716 | 550/530 | 670/606 |
| 2 weeks - 12/30 RPM | 510/496 | 390/368 | 370/356 |
| 4 weeks - 12/30 RPM | | 350/344 | |
| 8 weeks - 12/30 RPM | 430/412 | | 420/366 |
| 12 weeks - 12/30 RPM | 360/352 | | 370/360 |

What is claimed is:

1. An aqueous organic peroxide emulsion comprising:
    25-70 wt % organic peroxide, based on the weight of the emulsion,
    a droplet growth inhibitor comprising a cyclohexane dicarboxylate ester, wherein the cyclohexane dicarboxylate ester is present in an amount of 0.1-10 wt. %, based on the weight of the emulsion, and
    water.
2. Emulsion according to claim 1, wherein the cyclohexane dicarboxylate ester is di-isononyl cyclohexane dicarboxylate (DINCH).
3. Emulsion according to claim 1, additionally comprising an anti-freeze agent.
4. Emulsion according to claim 3, wherein the anti-freeze agent is selected from the group consisting of methanol, ethanol, isopropanol, glycols, propanediol, glycerol, and mixtures thereof.
5. The emulsion according to claim 4, wherein the water/anti-freeze agent weight ratio is from 3/1 to 2/1.
6. Emulsion according to claim 1, additionally comprising a protective colloid.
7. Emulsion according to claim 1, additionally comprising an emulsifier.
8. Emulsion according to claim 7, wherein the emulsifier is a non-ionic surfactant.
9. A method of polymerizing a vinyl chloride monomer wherein the emulsion according to claim 1 is added to a vinyl chloride monomer in an effective amount.
10. The aqueous emulsion according to claim 1, wherein the $99^{th}$ percentile of the droplet volume distribution of the organic peroxide does not exceed 15 microns during 12 weeks of storage at $-20°$ C.
11. The emulsion according to claim 1, wherein the cyclohexane dicarboxylate ester is present in an amount of 0.5-5 wt %, based on the weight of the emulsion.
12. The emulsion according to claim 1, wherein the organic peroxide is chosen from cumyl peroxyneodecanoate, tert-butyl peroxyneodecanoate, tert-butyl peroxyneoheptanoate, 1-(2-ethylhexyl-peroxy)-1,3-dimethylbutyl peroxypivalate, or di(3,5,5-trimethylhexanoyl) peroxide.
13. The emulsion according to claim 12, wherein the organic peroxide is present in an amount of from 40-60 wt %, based on the weight of the emulsion.
14. The emulsion according to claim 13, wherein the amount of water in the emulsion is from 20 to 70 wt %, based on the weight of the emulsion.
15. The emulsion according to claim 13, wherein the amount of water in the emulsion is from 25 to 40 wt %, based on the weight of the emulsion.
16. An aqueous organic peroxide emulsion comprising:
    25-70 wt % of an organic peroxide chosen from tert-butyl peroxyheptanoate, tert-butyl peroxyneodecanoate, tert-amyl peroxyneodecanoate and combinations thereof, based on the weight of the emulsion,
    0.5 to 2 wt % di-isononyl cyclohexane dicarboxylate, based on the weight of the emulsion,
    0.5 to 5 wt % of a protective colloid chosen from partially hydrolysed/saponified polyvinyl acetates, cellulose, cellulose derivatives, starch, starch derivatives, and combinations thereof;
    a non-ionic surfactant having a hydrophile-lipophile balance of 16 or higher,
    an anti-freeze agent chosen from methanol, ethanol, isopropanol, ethylene glycol, propanediol, glycerol, and mixtures thereof; and
    water,
    wherein a water/anti-freeze agent weight ratio is from 3/1 to 2/1.
17. The emulsion of claim 16 consisting of the organic peroxide, the di-isononyl cyclohexane dicarboxylate, the protective colloid, the non-ionic surfactant, the anti-freeze agent, and the water.
18. The emulsion of claim 16 consisting of:
    the organic peroxide present in an amount of 50 wt % based on the weight of the emulsion,
    the di-isononyl cyclohexane dicarboxylate present in an amount of 0.9 wt % based on the weight of the emulsion,
    the protective colloid present in an amount of 2.8 to 3 wt % based on the weight of the emulsion,
    the non-ionic surfactant present in an amount of 0.5 wt % based on the weight of the emulsion,
    the anti-freeze agent present in an amount of 12.5 to 12.7 wt % based on the weight of the emulsion; and
    the water.

19. The emulsion of claim 16 consisting of:
the organic peroxide present in an amount of 50 wt % based on the weight of the emulsion,
the di-isononyl cyclohexane dicarboxylate present in an amount of 0.9 wt % based on the weight of the emulsion,
the protective colloid which is polyvinylacetate having an average degree of hydrolysis of 62.5-67.5% and is present in an amount of 2.8 to 3 wt % based on the weight of the emulsion,
the non-ionic surfactant which is a C16/C18 ethoxylated alcohol and is present in an amount of 0.5 wt % based on the weight of the emulsion,
the anti-freeze agent which is methanol and is present in an amount of 12.5 to 12.7 wt % based on the weight of the emulsion; and
the water.

20. The emulsion of claim 16 consisting of:
the organic peroxide present in an amount of 50 wt % based on the weight of the emulsion,
the di-isononyl cyclohexane dicarboxylate present in an amount of 0.9 wt % based on the weight of the emulsion,
the protective colloid which is polyvinylacetate having an average degree of hydrolysis of 62.5-67.5% and is present in an amount of 2.8 to 3 wt % based on the weight of the emulsion,
the non-ionic surfactant which is a C16/C18 ethoxylated alcohol and is present in an amount of 0.5 wt % based on the weight of the emulsion,
the anti-freeze agent which is methanol and is present in an amount of 12.5 to 12.7 wt % based on the weight of the emulsion; and
the water present in an amount of 32.8 to 33.3 wt % based on the weight of the emulsion, and
wherein the $99^{th}$ percentile of the droplet volume distribution of the organic peroxide does not exceed 15 microns during 12 weeks of storage at −20° C.

* * * * *